US00PP17292P2

(12) United States Plant Patent
Thorup

(10) Patent No.: US PP17,292 P2
(45) Date of Patent: Dec. 19, 2006

(54) ***VERBENA* PLANT NAMED 'BALAZDAPIMA'**

(50) Latin Name: *Verbena×hybrida*
Varietal Denomination: Balazdapima

(75) Inventor: Troy Thorup, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 19 days.

(21) Appl. No.: 11/312,200

(22) Filed: Dec. 20, 2005

(51) Int. Cl.
*A01H 5/00* (2006.01)

(52) U.S. Cl. ..... Plt./308

(58) Field of Classification Search ..... Plt./308
See application file for complete search history.

(56) References Cited

PUBLICATIONS

European Plant Breeders' Rights application No. 2005/1960 filed Oct. 24, 2005.

*Primary Examiner*—Kent Bell
*Assistant Examiner*—Annette H Para
(74) *Attorney, Agent, or Firm*—Audrey Charles

(57) ABSTRACT

A new and distinct cultivar of *Verbena* plant named 'Balazdapima' characterized by its dark pink-colored flowers, medium green-colored foliage, good basal branching, and compact, spreading growth habit.

1 Drawing Sheet

Latin name of genus and species of plant claimed: *Verbena×hybrida.*
Variety denomination: 'Balazdapima'.

BACKGROUND OF THE INVENTION

The present invention relates to a new and distinct cultivar of *Verbena* plant botanically known as *Verbena×hybrida* and hereinafter referred to by the cultivar name 'Balazdapima'.

The new cultivar originated in a controlled breeding program in Guadalupe, Calif. during 2002. The object of the breeding program was the development of *Verbena* cultivars with attractive flower coloration, continuous flowering, small, dark green-colored foliage, excellent basal branching, and a spreading trailing growth habit.

The female (seed) parent of the new cultivar was the proprietary *Verbena×hybrida* breeding selection designated 905-5, not patented, characterized by its burgundy-colored flowers, and compact, well-branched growth habit. The male (pollen) parent of the new cultivar was the proprietary *Verbena×hybrida* breeding selection designated 957-4, not patented, characterized by its burgundy-colored flowers, and compact, well-branched growth habit. The new *Verbena* was discovered and selected by the inventor as a single flowering plant within the progeny of the above stated cross-pollination during the spring of 2003 in a controlled environment at Rijsenhout, the Netherlands.

Asexual reproduction of the new cultivar by terminal stem cuttings since the spring of 2003 at Rijsenhout, the Netherlands and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balazdapima' as a new and distinct cultivar of *Verbena* plant:

1. Dark pink-colored flowers;
2. Medium green-colored foliage;
3. Good basal branching; and
4. Compact, spreading growth habit.

Plants of the new cultivar differ from plants of the female parent primarily in flower color and from plants of the male parent primarily in flower color.

Of the many commercially available *Verbena* cultivars known to the inventor, the most similar in comparison to the new cultivar is 'Balwilrose', U.S. Plant Pat. No. 12,927. However, in side by side comparisons, plants of the new cultivar differ from plants of 'Balwilrose' in the following characteristics:

1. Plants of the new cultivar are shorter than plants of 'Balwilrose';
2. Plants of the new cultivar are wider than plants of 'Balwilrose'; and
3. Plants of the new cultivar have smaller inflorescences than plants of 'Balwilrose'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balazdapima'. The plants were grown in 10 cm pots for 13 weeks in a greenhouse at West Chicago, Ill.

DETAILED BOTANICAL DESCRIPTION

Figure 1:
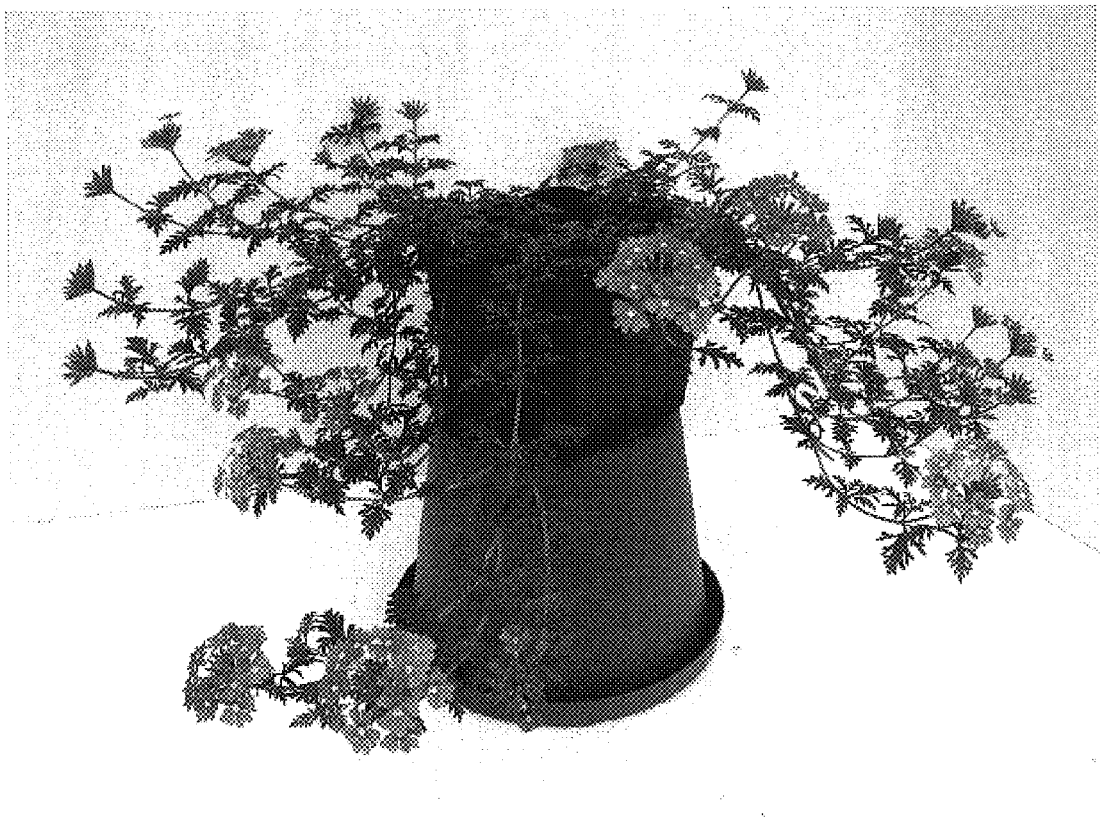
FIG. 1 illustrates a side view of the overall growth and flowering habit of 'Balazdapima'.
Figure 2:
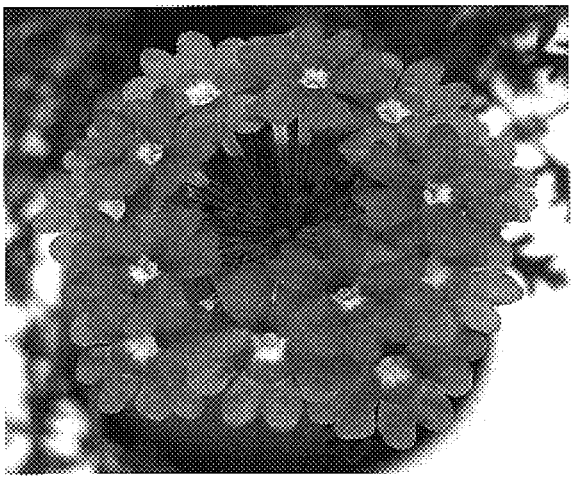
FIG. 2 illustrates a close-up view of a single inflorescence of 'Balazdapima'.
Figure 3:
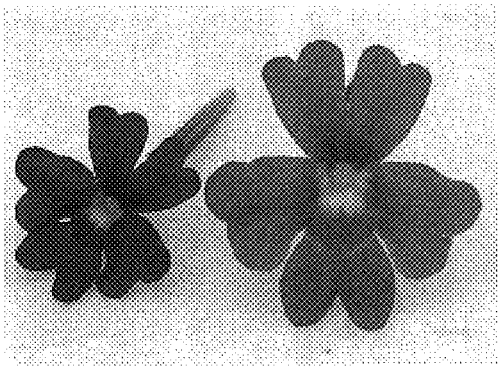
FIG. 3 illustrates a close-up view of a single flower of 'Balazdapima'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 25, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 13 weeks utilizing a soilless growth medium. Greenhouse temperatures were maintained at approximately 70° F. to 80° F. (21° C. to 26° C.) during the day and approximately 62° F. to 65° F. (17° C. to 18° C.) during the night. Greenhouse light levels of 5,000 to 8,000 footcandles were maintained during the day.

Botanical classification: *Verbena×hybrida* cultivar Balazdapima.

Parentage:

*Female parent.*—Proprietary *Verbena×hybrida* breeding selection designated 905-5, not patented.

*Male parent.*—Proprietary *Verbena×hybrida* breeding designated 957-4, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Crop time.*—Approximately 5 to 7 weeks from a rooted cutting.

*Growth habit and general appearance.*—Compact, spreading.

*Size.*—Height from soil level to top of plant plane: Approximately 5.7 cm. Width: Approximately 61.4 cm.

*Branching habit.*—Freely basal branching. Approximately 8 main branches per plant with lateral branches potentially forming at every node.

*Branch.*—Shape: Square in cross section. Strength: Strong. Length: Approximately 32.4 cm. Diameter: Approximately 1.8 mm. Texture: Hispid. Color: 144B with 59A along edges. Internode length at center of branch: Approximately 2.5 cm.

*Foliage.*—Number of leaves per main branch: Approximately 24. Fragrance: None. Form: Simple. Arrangement: Opposite. Aspect: At right to acute angle to stem. Shape: Ovate. Margin: Lobed. Apex: Acute. Base: Attenuate. Venation pattern: Pinnate. Length of mature leaf: Approximately 3.2 cm. Width of mature leaf: Approximately 2.2 cm. Texture of upper surface: Hirsute. Texture of lower surface: Glabrous except hirsute along veins. Color of upper surface of young and mature foliage: 137A with venation of 145A. Color of lower surface of young and mature foliage: 137C with venation of 145B. Petiole length: Approximately 9.1 mm. Petiole diameter: Approximately 1.8 mm. Petiole texture: Hirsute. Petiole color: 145B.

Flowering description:

*Flowering habit.*—'Balazdapima' is freely flowering under outdoor growing conditions with substantially continuous blooming from spring through autumn and year round in greenhouse environment.

*Time to first flower.*—Approximately 10.3 weeks from sticking of unrooted cutting.

*Lastingness of individual bloom.*—Approximately 5 to7 days.

Inflorescence description:

*Type.*—Corymb. Quantity per plant: Approximately 9 at 13 weeks. Length/Height: Approximately 2.3 cm. Width: Approximately 4.6 cm. Quantity of fully opened flowers per inflorescence at any one time: Approximately 14.

*Peduncle.*—Strength: Strong. Aspect: Erect. Length: Approximately 2.0 cm. Diameter: Approximately 1.1 mm. Texture: Hispid. Color: 144B.

Flower description:

*Type.*—Sessile, salverform. Fragrance: None.

*Bud rate of opening.*—Generally takes 3 to 6 days for bud to progress from first color to fully open flower.

*Bud just before opening.*—Shape: Elongated, globular. Length: Approximately 3.0 mm. Diameter: Approximately 3.0 mm. Color: Closest to 60B.

*Corolla.*—Shape: Round. Diameter: Approximately 1.6 cm. Depth: Approximately 4.0 mm.

*Petals.*—Quantity: 5, fused at base forming a tube. Appearance: Velvety. Aspect: Flat. Shape: Obovate. Apex: Emarginate. Margin: Entire. Texture of upper surface: Glabrous. Texture of lower surface: Glabrous to puberulent. Length of upper petal from tube: Approximately 7.8 mm. Width of upper petal: Approximately 7.3 mm. Length of lateral petal from tube: Approximately 7.6 mm. Width of lateral petal: Approximately 6.9 mm. Length of lower petal from tube: Approximately 7.3 mm. Width of lower petal: Approximately 5.1 mm. Color of upper surface when fully open: N74B. Color of lower surface when fully open: N74C. Whiskers of 150D surround the opening of the corolla tube.

*Corolla tube.*—Length: Approximately 1.7 cm. Diameter at corolla: Approximately 2.0 mm. Diameter at base: Approximately 1.0 mm. Texture of inner surface: Densely pubescent. Texture of outer surface: Glabrous with moderate pubescence at distal end. Color of inner and outer surfaces: 155A with 145C at distal end.

*Calyx.*—Shape: Tubular, with 5 acute tips. Length/Depth: Approximately 1.2 cm. Width: Approximately 2.1 mm.

*Sepals.*—Quantity per flower: 5. Shape: Lanceolate. Apex: Acuminate. Margin: Fused. Sepal length: Approximately 1.2 cm. Sepal width: Approximately 1.3 mm. Texture: Densely pubescent with a mixture of glandular and non-glandular hairs. Gland color: 79A. Color of upper or inner surface: 144A. Color of lower or outer surface: 144A with N77B along margins of apex. Stipule shape: Lanceolate. Stipule apex: Acuminate. Stipule length: Approximately 4.3 mm. Stipule width at base: Approximately1.8 mm. Stipule texture: Densely pubescent with a mixture of glandular and non-glandular hairs. Stipule gland color: 79A. Stipule color: 144B.

*Reproductive organs.*—Androecium: Stamen quantity: 4. Stamen length: Approximately 1.0 mm. Anther shape: Ovate, bilobed. Anther length: Approximately 0.8 mm. Anther color: N144C. Pollen amount: None observed. Gynoecium: Pistil quantity: One per flower. Pistil length: Approximately 1.9 cm. Stigma shape: Funnel. Stigma length: 2.5 mm. Stigma color: 144A. Style length: Approximately 1.5 cm. Style color: 144C. Ovary diameter: Approximately 1.5 mm. Ovary texture: Glabrous. Ovary color: 144B.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balazdapima', substantially as herein shown and described.

* * * * *